United States Patent [19]

Lovley

[11] Patent Number: 4,886,752

[45] Date of Patent: Dec. 12, 1989

[54] MICROBIAL PRODUCTION OF ULTRAFINE-GRAINED MAGNETITE

[75] Inventor: Derek R. Lovley, Paris, Va.

[73] Assignee: The United States of America as represented by the Secretary of the Interior, Washington, D.C.

[21] Appl. No.: 248,220

[22] Filed: Sep. 23, 1988

[51] Int. Cl.[4] .......................... C12P 3/00; C12P 1/04; C12R 1/01; C12N 1/22

[52] U.S. Cl. .................................... 435/168; 435/170; 435/154; 435/252.1; 435/801; 435/822

[58] Field of Search ............... 435/168, 154, 131, 170, 435/252.1, 822, 801

[56] References Cited

U.S. PATENT DOCUMENTS

| | | | |
|---|---|---|---|
| 4,385,119 | 5/1983 | Blakemore | 435/168 |
| 4,394,451 | 7/1983 | Blakemore et al. | 435/168 |
| 4,432,998 | 2/1984 | Peer | 435/170 |
| 4,677,067 | 6/1987 | Schwartz et al. | 435/820 |

FOREIGN PATENT DOCUMENTS

| | | | |
|---|---|---|---|
| 0172288 | 9/1985 | Japan | 435/168 |
| 2040299 | 2/1987 | Japan | 435/173 |
| 2061599 | 3/1987 | Japan | 435/173 |
| 2134083 | 6/1987 | Japan | 435/243 |
| 2192870 | 1/1988 | United Kingdom | 435/168 |

*Primary Examiner*—Herbert J. Lilling
*Assistant Examiner*—Stephanie W. Zitomer
*Attorney, Agent, or Firm*—E. Philip Koltos

[57] ABSTRACT

A method of producing magnetite is disclosed which comprises culturing a microorganism designated GS-15 in the presence of organic matter and a ferric iron compound. Unlike prior art production of magnetite using magnetotactic bacteria, GS-15 is able to produce large amounts of ultrafine-grained magnetite extracellularly under anaerobic conditions, allowing for easy separation and recovery of the magnetite without the need for rigorous control over oxygen tensions in the culture medium. As a result, the method of the present invention can be used to mass produce magnetite efficiently using inexpensive means and materials.

11 Claims, No Drawings

MICROBIAL PRODUCTION OF ULTRAFINE-GRAINED MAGNETITE

BACKGROUND OF THE INVENTION

The invention relates to a method of producing magnetite by culturing a microorganism designated GS-15 in the presence of organic matter and ferric iron.

Magnetite ($Fe_3O_4$) is a mineral of great commercial value in that it is useful, e.g., in magnetic recording devices and as toner for plain paper copiers. Particularly desirable for these purposes is magnetite in ultrafine-grained (roughly 20–50 nanometers in diameter) form. It has recently been discovered that biologically pure cultures of a magnetotactic bacterium designated "MS-1" can be used to synthesize ultrafine-grained magnetite. In U.S. Pat. No. 4,385,119 (Blakemore), it is disclosed that a magnetotactic bacterium of the genus Aquaspirillum contains intracellular chains of single domain magnetite particles, and that these particles can be recovered from cultures of the bacterium and employed for the purposes described above. Methods of culturing the magnetotactic bacteria and removing the products produced therein are disclosed in U.S. Pat. No. 4,394,451 (Blakemore et al) and U.S. Pat. No. 4,677,067 (Schwartz et al), respectively.

Unfortunately, the method of producing useful magnetite particles through culturing microorganisms as described in the above patents is extremely impractical for a number of reasons. First, these organisms are very difficult to culture in large quantities. Second, the amount of magnetite produced in each cell is extremely small (only about 20 crystals), and this further limits the total amount of magnetite that can be recovered. Third, under processes carried out with magnetotactic bac-bacteria, the oxygen tensions which are applied to the culturing medium have to be very carefully controlled in order to ensure that only magnetite-bearing bacteria will be cultured. Finally, the magnetite crystals are produced intracellularly in bacterium MS-1 and as such will stay bound within the organism, thus requiring extensive purification and recovery procedures in order to obtain pure magnetite.

It would thus be desirable to develop a microbial process which produces ultrafine-grained magnetite extracellularly so that it is readily separable and recoverable from a culture medium. It is also desirable that the microbe used in such a process be able to produce copious qualities of magnetite, and that such a microbe be readily grown in mass culture using inexpensive materials.

SUMMARY OF THE INVENTION

It has been discovered that magnetite can be produced inexpensively and in large amounts by culturing a microorganism recovered from river sediments and designated "GS-15" in the presence of organic matter and a ferric iron compound. Unlike magnetotactic bacteria, GS-15 produces magnetite extracellularly through the reduction of ferric iron which is coupled to the oxidation of organic matter during the microorganism's metabolic processes. As a result, the extracellular magnetite, produced in the desired ultrafine-grained form, is easily separated from the bacterial cells and readily recovered. Additionally, the cells of GS-15 can be readily grown in mass cultures using cheap materials such as acetic acid and ferric oxide. A further advantage is derived in that this process is carried out anaerobically, and a precise control over oxygen tensions is not needed in order to produce the magnetite.

DETAILED DESCRIPTION OF THE PREFERRED EMBODIMENTS

Although microbial reduction of ferric iron plays an important role in the iron geochemistry and organic matter mineralization of aquatic sediments, the pathways for organic matter metabolism and the organisms which carry out these reactions are only recently beginning to be identified. Previous studies in this area described bacteria which reduced ferric iron during anaerobic growth, but only as a minor reaction, with fermentation being the major mode of organic matter metabolism. It has now been discovered that microorganism GS-15 is the first organism to effectively couple organic matter oxidation to ferric iron reduction during growth under anaerobic conditions. GS-15, which has been deposited in the American Type Culture Collection 12301 Parklawn Drive, Rockville, Md. and has received accession No. 53774, was isolated from sediments recovered from the Potomac River.

The coupling of organic matter oxidation and ferric iron reduction during metabolism allows for microorganism GS-15 to produce great amounts of magnetite efficiently and cheaply. When acetate is supplied to the bacteria as organic matter, two moles of carbon dioxide are produced and eight moles of ferric iron are reduced to ferrous iron for every mole of acetate oxidized by GS-15. Because iron serves as the terminal electron acceptor for metabolism, this reduction is termed dissimilatory iron reduction to distinguish it from the reduction of iron during microbial assimilation of intracellular iron. It will be clear to one skilled in the art that organic matter as used in this application refers to any of a number of suitable carbon compounds which are conventionally employer in the culturing of bacteria, particularly those compounds having from 1 to 12 carbon atoms. In addition to acetate or acetic acid, organic matter particularly suited for use in the present invention includes compounds such as ethanol, butyrate and propionate.

When grown or cultured in suitable media under anaerobic conditions, the dissimilatory iron reduction by GS-15 results in the formation of a highly magnetic black precipitate. A preferred medium for growing GS-15 contains acetate, provided in the form of acetic acid, various major and minor minerals, and approximately 0.2 moles of ferric iron per liter provided in the form of amorphic ferric oxide. The medium contains no reducing agents, and the acetate is the sole electron donor. The oxygen can be removed from the media in any of a number of ways known in the art, but it is preferred to remove oxygen by degassing the media with nitrogen. The temperature is preferably kept at from around 25°–40° C. (30°–35° C. particularly preferred) since it has been observed that higher temperatures (e.g., around 50° C.) inhibit production of the black precipitate. The pH is maintained at from about 6.0 to 8.0, with 6.5 to 7.5 being the preferred range.

The cultured GS-15 was able to produce large amounts of the highly magnetic black precipitate, and this precipitate was readily separated from the bacterial cells by conventional means and isolated for experimental analysis. Both electron diffraction patterns from precipitate crystals and magnetometer tests on the recovered precipitate indicated that the produced material was magnetite. A further test with sodium dithionite-citrate solution confirmed this analysis.

Examination of the magnetite produced by GS-15 was conducted using transmission electron microscopy (TEM). The TEM examination revealed aggregates of small crystals of ultrafine-grained magnetite which ranged in size from about 10 to 5 nanometers. The crystals were observed to be clearly external of the GS-15 cells and were not aligned in chain structures. Further evidence of the extracellular nature of magnetite production was provided in wet mount tests where isolated GS-15 cells (without precipitate), unlike magnetotactic bacteria, did not orient in response to an applied magnetic field.

The results of these studies have shown that the non-magnetotactic GS-15 bacterium can produce large quantities of ultrafine-grained magnetite extracellularly by coupling oxidation or organic matter with reduction of ferric iron compounds under anaerobic conditions. By the method of the present invention, therefore, a new and inexpensive source of ultrafine-grained magnetite is now provided.

The following example is presented as illustrative of the present invention and is not intended to restrict its scope in any way.

EXAMPLE

The microorganism GS-15 was cultured in a medium containing (in grams per liter of deionized water): $CaCl_2 \cdot 2H_2O$, 0.1; KCl, 0.1; $NH_4Cl$, 1.5; $NaH_2PO_4 \cdot H_2O$, 0.6; sodium acetate, 6.8; nitrilotriacetic acid, 0.015; $MgSO_4$, 0.03; $MnSO_4$, 0.005; NaCl, 0.01; $FeSO_4$, 0.001; $CaCl_2$, 0.001; $CoCl_2$, 0.001; $ZnCl_2$, 0.001; $CuSO_4$, 0.0001; $AlK(SO_4)_2$, 0.0001; $H_3BO_3$, 0.0001; $Na_2Mo_4$, 0.0025; $NiCl_2 \cdot 6H_2O$, 0.00024; $Na_2WoO_4$, 0.00025; biotin, $2 \times 10^{-5}$; folic acid, $2 \times 10^{-5}$; pyridoxine hydrochloride, $1 \times 10^{-4}$; thiamine, $5 \times 10^{-5}$; riboflavin, $2 \times 10^{-5}$; nicotinic acid, $5 \times 10^{-5}$; calcium panthothenate, $5 \times 10^{-5}$; tamin $B_{12}$, $1 \times 10^{-7}$; p-aminobenzoic acid, $5 \times 10^{05}$; and thiotic acid, $5 \times 10^{-5}$; The medium contained 250 mmoles of Fe(III) per liter in the form of amorphic Fe(III) oxide. The amorphic ferric oxide was prepared by neutralizing a 0.4 molar solution of ferric chloride to pH 7 with NaOH and then washing the amorphic ferric oxide precipitate to remove salts. Oxygen was removed from the medium by degassing with nitrogen and the medium was maintained under a nitrogen atmosphere during the growth of the organism. The pH of the autoclaved (121° C., 20 minutes) medium was 7.0. At 30° C., the metabolism of GS-15 resulted in the production of approximately 75 millimoles of magnetite per liter of this medium.

GS-15 produced magnetite at acetate concentrations ranging from 10 to 100 millimoles per liter and also could produce magnetite with ethanol, butyrate, or propionate as the substrate at concentrations of 10 or 20 millimoles per liter of medium.

During the growth of GS-15, the microorganism converted the non-magnetic brown amorphic ferric oxide to a black solid material which was strongly attracted to a magnet. In other tests to isolate the origin of this material, the black precipitate was not formed in the culture medium if the medium was not inoculated with GS-15. In addition, if the culture was incubated at temperatures too high for microbial growth (e.g., 50° C.), or if the inoculated medium was sterilized prior to incubation, the precipitate was not formed. In cases where ferrous iron compounds were added to uninoculated medium, again no black precipitate was formed. These results indicated specifically that the metabolism of GS-15 was necessary for the formation of the precipitate.

The black precipitate was identified as magnetite in a number of ways. A selected area electron diffraction pattern was taken from an aggregate of precipitate crystals, and the results showed a diffuse ring pattern along with a few single crystal diffraction spots. This diffraction pattern was characteristic of magnetite. The black precipitate was treated with a sodium dithionite-citrate solution which dissolves hematite, maghemite, goethite and pyrrhotite, but not magnetite. The precipitate did not dissolve in the sodium dithionite-citrate solution.

The black precipitate produced by the culturing of GS-15 was also identified as magnetite through a series of tests of its magnetic properties as determined using a SQUID magnetometer. Anhysterhetic remanent magnetization (ARM) in a biasing field of 2.5 G with subsequent alternating field demagnetization (AF) was followed by saturation isothermal remanent magnetization (sIRM) and AF demagnetization. The coercivity spectrum generated was indicative of a ferromagnetic mineral like magnetite and is similar to the coercivity spectra observed in marine sediments known to contain ultrafine-grained magnetite. A Lowrie-Fuller test was performed by comparing the values for the median destructive field (MDF, peak field at 50% sIRM) of the AF of sIRM and AF of ARM. The $MDF_{ARM}$ was greater than $MDF_{sIRM}$, and this suggests that the particles are magnetically of single domain.

There was also strong evidence that the magnetite produced in the GS-15 culture media was extracellular. Examination of the black precipitate with transmission electron microscopy (TEM) revealed aggregates of small crystals ranging in size from 10 to 50 nm. These crystals were clearly observed to be external to the GS-15 cells, and were not aligned in chains. Tests for the presence of intracellular magnetite were carried out by wet mounting GS-15 bacterial cells, and observing their pattern in response to an applied magnetic field. Under these conditions, magnetotactic bacteria having intracellular magnetite were observed to orient in response to the magnetic field. The wet mounts of GS-15 did not orient when a magnetic field was applied, further indicating that the magnetite produced by GS-15 was extracellular, and not intracellular.

These tests indicated that cultured media containing GS-15, organic matter, and ferric iron, would be able to produce amounts of extracellular, ultrafine-grained magnetite in ample quantities, and in a form more easily separable and recoverable that prior art methods involving magnetotactic bacteria.

What is claimed is:

1. A method of producing magnetite comprising culturing under anaerobic conditions a non-magnetotactic microorganism designated GS-15 and deposited at the American Type Culture Collection, bearing accession No. 53774, in the presence of a suitable carbon compound and a ferric iron compound.

2. A method according to claim 1 wherein the magnetite is produced extracellularly by the microorganism GS-15.

3. A method according to claim 1 wherein the carbon compound comprises an acetate.

4. A method according to claim 1 wherein the carbon compound comprises acetic acid.

5. A method according to claim 1 wherein the carbon compound is selected from the group consisting of ethanol, butyrate and propionate.

6. A method according to claim 1 wherein the ferric iron compound comprises ferric oxide.

7. A method according to claim 1 which is carried out at a temperature of from about 25° to 40° C.

8. A method according to claim 1 which is carried out at a pH of from about 6.0 to 8.0.

9. A method according to claim 1 wherein the magnetite produced is ultrafine-grained.

10. A method according to claim 9 wherein the magnetite has grains of from about 10 to 50 nanometers in diameter.

11. A method according to claim 1 wherein the carbon compound has from 1 to 12 carbon atoms.

* * * * *